(12) United States Patent
Kondo

(10) Patent No.: US 6,545,272 B1
(45) Date of Patent: Apr. 8, 2003

(54) APPARATUS AND METHODS FOR MONITORING CONTAMINATION OF AN OPTICAL COMPONENT IN AN OPTICAL SYSTEM

(75) Inventor: Hiroyuki Kondo, Kawasaki (JP)

(73) Assignee: Nikon Corporation, Tokyo (JP)

( * ) Notice: Subject to any disclaimer, the term of this patent is extended or adjusted under 35 U.S.C. 154(b) by 274 days.

(21) Appl. No.: 09/587,626

(22) Filed: Jun. 5, 2000

(30) Foreign Application Priority Data

Jun. 7, 1999 (JP) .......................................... 11-159020

(51) Int. Cl.⁷ .............................................. G01N 21/88
(52) U.S. Cl. ........................ 250/305; 250/492.2; 378/34
(58) Field of Search .............................. 250/305, 492.2; 378/34

(56) References Cited

U.S. PATENT DOCUMENTS 3,965,351 A * 6/1976 Strongin et al. ............ 250/305
5,138,158 A * 8/1992 Ninomiya et al. .......... 250/305
5,393,980 A * 2/1995 Yost et al. ................... 250/305
5,569,916 A * 10/1996 Tomie ......................... 250/305

* cited by examiner

Primary Examiner—Jack Berman
(74) Attorney, Agent, or Firm—Klarquist Sparkman LLP

(57) ABSTRACT

Apparatus and methods are disclosed for measuring the state of contamination of one or more optical components in an optical system, such as in an X-ray optical system. Also disclosed are microlithography systems including a device for monitoring accumulation of a contaminant substance on a surface of an optical component of the system. The optical component is irradiated with a beam of electromagnetic radiation or a beam of charged particles (e.g., electron beam). The state of contamination of the optical component is measured by detecting electrons emitted from the optical component as the optical component is being irradiated with the beam. Electrons are quantified that are within a specified energy range of emitted electrons.

43 Claims, 5 Drawing Sheets

APPARATUS AND METHODS FOR MONITORING CONTAMINATION OF AN OPTICAL COMPONENT IN AN OPTICAL SYSTEM

FIELD OF THE INVENTION

The present invention pertains to monitoring apparatus that detect the state of contamination of optical components of an optical system (e.g., microscope, analysis device, or microlithography apparatus) that utilizes electromagnetic radiation such as X-rays or ultraviolet light, or a charged particle beam. The invention also pertains to optical systems (e.g., microscope, analysis device, or microlithography apparatus) including such a monitoring apparatus. The invention also pertains to microlithography methods including contaminant-monitoring of certain optical components.

BACKGROUND OF THE INVENTION

X-rays produced by synchrotron radiation have high brightness and variable wavelength, and hence are used as X-ray sources for X-ray analysis devices, X-ray microscopes, and X-ray microlithography (projection-exposure) apparatus. Another useful X-ray source is a laser-plasma X-ray source (abbreviated "LPX" source). In an LPX source, a pulsed laser light beam is focused onto a target substance contained inside a vacuum chamber. The pulses of laser light impinging on the target substance create a plasma that emits X-rays. The X-rays radiating from the plasma are extracted and formed into an X-ray beam. LPX sources have a brightness comparable to that of synchrotron sources, and have the advantage of compactness. Consequently, LPX sources have been under intensive development recently as the X-ray source of choice for various applications.

Other X-ray sources that are attracting attention utilize a so-called "Z-pinch" plasma, dense plasma focus, or plasma created by a discharge in a capillary. These sources are relatively inexpensive.

In an X-ray microlithography apparatus, a reticle (defining a pattern) is irradiated by an X-ray beam from a source. After irradiating the reticle, the X-ray beam is manipulated and directed to form a corresponding image of the pattern on a suitable substrate (e.g., semiconductor wafer) previously "sensitized" with a coating of an appropriate "resist." The X-ray beam is manipulated and directed using X-ray optical components (mainly specialized mirrors). The wavelength of X-rays used in conventional X-ray microlithography apparatus is in the extreme ultraviolet region, having a wavelength in the range of a few nanometers to approximately 50 nanometers. These X-rays are termed "soft" X-rays. Since many substances are highly absorptive to radiation in this range of wavelengths, adhesion of even a slight amount of a contaminant substance to an X-ray optical component can cause a conspicuous deterioration in the optical characteristics (e.g., reflectivity and transmissivity) of the X-ray optical component.

In optical devices that use soft X-rays, the optical path typically is evacuated to high vacuum to eliminate attenuation of the X-rays by the atmosphere. Accordingly, the X-ray optical components are enclosed in a vacuum chamber, and the interior of the vacuum chamber is evacuated to high vacuum using a suitable vacuum device such as a rotary-vane pump or diffusion pump, etc. Unfortunately, these vacuum devices tend to produce a slight back-flow of pump-oil vapor into the vacuum chamber during operation, thereby introducing oil molecules into the vacuum chamber.

Also, the resist tends to outgas in a vacuum. With extended operation, these introduced oil molecules and resist-outgas molecules tend to accumulate on the X-ray optical components inside the vacuum chamber, causing progressive deterioration of the optical characteristics of the X-ray optical components.

In addition, LPX and discharge-plasma X-ray sources tend to produce particulate debris from the plasma and/or from structures located near the plasma. The debris can adhere to a nearby X-ray optical component, causing the optical characteristics of the optical component to deteriorate. Such deterioration can result in a decline in throughput of the apparatus itself.

In conventional microlithography apparatus, there currently is no practical technique with which to monitor the degree of contamination of the optical components during operation of the apparatus. Rather, whenever an exposure dosage applied to the object of irradiation has degraded to an insufficient level from repeated or prolonged operation of the apparatus, contamination of the optical components is suspected and corrective action taken.

For example, in the case of an X-ray microscope employing an LPX source, ten "shots" normally are required to obtain a clear image. Whenever the number of shots required to obtain a suitably clear image increases to, say, 20 shots, the X-ray optical components of the microscope are deemed to be excessively contaminated. In X-ray microlithography apparatus, the constituent X-ray optical components are deemed contaminated when the time required to achieve transfer of a pattern having a certain minimum linewidth becomes excessively long.

In each of the foregoing methods, the presence or absence of contamination of the optical components is adjudged only after the contamination has begun to exert a large adverse influence on operation of the apparatus. In other words, the presence or absence of contamination of the optical components is unknown until the effects of contamination are manifest to an apparent unacceptable degree.

SUMMARY OF THE INVENTION

In view of the problems of the prior art, as summarized above, an object of the present invention is to provide apparatus and methods with which the state of surficial contamination of an optical component in an optical system is measured. Another object is to provide any of various optical systems, such as an X-ray microlithography apparatus, with which one or more constituent optical components can be monitored for contaminant accumulation so as to allow the need for cleaning or replacement of the optical component to be determined.

To such ends, and according to a first aspect of the invention, apparatus are provided for measuring accumulation of a contaminant substance on a surface of an optical component that, during use, is irradiated with radiation. An embodiment of such an apparatus comprises a contaminant-measuring means situated and configured to perform several tasks. First, the contaminant-measuring means detects electrons emitted by the optical component in response to the optical component being irradiated with the radiation. Of the detected electrons, the contaminant-measuring means selects electrons in a specified energy range, and obtains a measurement of the detected electrons in the specified energy range so as to obtain a measurement of a corresponding amount of accumulated contaminant substance on the optical component. An exemplary measurement is of the quantity of electrons in the specified energy range.

In this apparatus, the radiation can be electromagnetic radiation (e.g., X-rays or ultraviolet radiation) or charged-particle-beam radiation (e.g., an electron beam) sufficient to cause emission of electrons (e.g., photoelectrons and/or Auger electrons) from a surface of the optical component irradiated with the radiation.

The apparatus also can include means for irradiating the optical component. Such means can be, for example, an X-ray optical system situated and configured to direct an X-ray beam from a source to the optical component.

The contaminant-measuring means can comprise detection means for detecting electrons emitted from the optical component, wherein the detection means produces an output signal having a parameter corresponding to a detected parameter of the electrons within the specified energy range. The detected parameter can be, for example, time of flight of the electrons. Generally, the number of electrons emitted from the optical component changes (typically is reduced) whenever a contaminant substance accumulates on the optical component. Hence, the contaminant-measuring means is configured such that the state of contamination of the optical component is detected by measuring the quantity of electrons in the specified energy range.

Typically, such as in an X-ray optical system, the optical component is a reflective component that comprises a surficial material. In such an instance, the energy range can be specified based on a characteristic of the surficial material and on an energy parameter of the radiation impinging on the surficial material. Alternatively or in addition, the energy range can be specified based on a particular contaminant substance predicted to adhere to the optical component.

Further alternatively, the contaminant-measuring means can comprise a substance-identification means configured to produce a spectrum of detected electrons in the specified energy range. The spectrum, in such a configuration, can be based on the surficial material, the particular contaminant substance that could adhere to the surficial material, and on an energy parameter of the radiation. In general, the bond energy of electrons varies according to the particular irradiated substance from which the electrons are emitted. Hence, electrons emitted in response to incident radiation (e.g., electromagnetic radiation) having a particular frequency have a different energy according to the particular substance. This difference allows contaminant accumulation to be monitored readily.

The substance-identification means can be configured to identify the contaminant substance by evaluating respective positions and magnitudes of one or more spectral peaks in the spectrum. The specified energy range can include a first energy range based on a characteristic of the surficial material and on an energy parameter of the radiation, and a second energy range based on a particular contaminant substance predicted to adhere to the optical component and on the energy parameter of the radiation. In the latter configuration, the substance-identification means is configured to determine respective numbers of electrons in each of the first and second energy ranges.

The contaminant-measuring means can be configured to detect electrons in the first energy range so as to produce a first signal, and to detect electrons in the second energy range so as to produce a second signal. The contaminant-measuring means in this configuration obtains a measurement of a state of contamination of the optical component by comparing the first and second signals.

The contaminant-measuring means can comprise detection means with which electrons are detected that are emitted within a specified angular range from the optical component. The detection means produces an output signal having a parameter corresponding to a detected parameter of the electrons within the specified energy range. In such a configuration, the contaminant-measuring means can comprise means for varying a detection angle of said detection means relative to the optical component.

Generally, the distance in which electrons emitted from a substance can pass through a physical object and escape without undergoing inelastic scattering depends on the energy of the emitted electrons. Accordingly, whenever electrons are emitted in a direction perpendicular to the surface of the substance, it is possible to measure electrons that are emitted from locations deeper within the substance than otherwise possible with electrons emitted at other angles relative to the surface. Hence, the depth at which emitted electrons can be detected can be varied by varying the detection angle of the detection means.

The optical component (e.g., X-ray mirror, filter, reticle, etc.) can be provided with a surficial material that emits electrons of a specified energy whenever the optical component is irradiated. For example, if emission of electrons does not occur from an optical component of interest, the optical component can be provided with a surficial layer of a substance having a lower bond energy than the material initially on the surface of the component. Hence, the optical component now can be monitored.

Another embodiment of an apparatus for measuring accumulation of a contaminant substance on a surface of an optical component comprises a detector and a processor. The detector is situated relative to the optical component so as to receive electrons emitted by the optical component in response to the optical component being irradiated with the radiation. The detector is configured to detect the electrons emitted from the optical component and produce a corresponding output signal. The processor is connected to the detector, and is configured to select, for data processing by the processor, at least a portion of the output signal corresponding to detected electrons in a specified energy range. The processor also obtains a measurement of the detected electrons in the selected energy range. As noted above, the electrons can be photoelectrons and/or Auger electrons.

In this embodiment, the specified energy range can be determined based on a characteristic of a material from which the optical component is made and on an energy characteristic of the radiation. For example, the optical component can be a multi-layer mirror, in which instance the material is configured as an outermost layer of the mirror.

As noted with the previous embodiment summarized above, the specified energy range can be determined based on a characteristic of a contaminant substance predicted to attach to the optical component and on an energy characteristic of the radiation. The detector can comprise a substance identifier that produces a spectrum of electrons within the specified energy range. In the latter instance, the specified energy range can be determined based on a characteristic of a material from which the optical component is made, and the processor can be configured to determine peak values within the spectrum and to identify the contaminant substance adhering to the optical component from the peak values of the spectrum.

The processor can be a computer and/or can comprise discrete portions. For example, the processor can comprise a signal processor, a selector, a comparator, and a memory. The signal processor is configured to process the output signal from the detector. The selector is connected to the signal processor and is configured to determine the specified energy range. The comparator is connected to the selector and is configured to compare a detected quantity of electrons in the specified energy range to a threshold value. The memory is connected to the comparator and is configured to store data corresponding to the threshold value.

According to another aspect of the invention, methods are provided for, with respect to an optical system comprising an optical component that is irradiated with radiation during use, measuring accumulation of a contaminant substance on the irradiated surface of the optical component. In an embodiment of the method, a beam of radiation is directed to impinge on the surface. The radiation desirably is of a quality that causes the surface to emit electrons in response to being irradiated with the radiation. Electrons emitted from the irradiated surface are detected. Of the detected electrons, electrons are selected that are in a specified energy range. The detected electrons in the specified energy range are measured so as to obtain a measurement of a corresponding amount of accumulated contaminant substance on the surface. The beam comprising the radiation can be a beam of electromagnetic radiation such as X-rays or ultraviolet light, or a beam of charged particles such as an electron beam.

In the above-summarized method, the step of measuring the detected electrons can be performed first and second times, wherein the second time is later than the first time and the optical component is used between the first and second times. In such an instance, the method can further comprise the step of comparing respective measurements of electrons obtained in the first and second times.

Alternatively, the step of measuring the detected electrons can comprise comparing a detected quantity of electrons in the specified energy range to a threshold value, and determining whether the detected quantity exceeds the threshold value.

Further alternatively, the step of measuring the detected electrons can comprise producing a spectrum of detected electrons in the specified energy range, and evaluating respective positions and magnitudes of one or more spectral peaks in the spectrum. In this embodiment, electrons can be selected in both a first energy range and in a second energy range. The first energy range can be based on a characteristic of a material from which the surface is made, and the second energy range can be based on a characteristic of a contaminant substance predicted to adhere to the optical component during use. In such an instance, respective numbers of electrons in each of the first and second energy ranges are determined. The method can further include the step of comparing the respective detected numbers of electrons in the first and second energy ranges.

Yet another aspect of the invention is utilized in optical apparatus in which the surface of an object is irradiated with X-rays or other radiation capable of causing an irradiated surface to emit electrons. Specifically, in this aspect, a device is provided for monitoring accumulation of a contaminant substance on an optical component of the optical apparatus. An embodiment of the device comprises an illumination-optical system, a detector, and a processor. The illumination-optical system is situated and configured to direct a beam of radiation (e.g., X-rays) from a radiation source along a trajectory leading to the optical component. The detector is situated relative to the optical component so as to receive electrons emitted by the optical component in response to the optical component being irradiated with the beam of radiation. The detector is configured to detect the electrons emitted from the optical component and produce a corresponding output signal. The processor is connected to the detector, and is configured to select at least a portion of the output signal corresponding to detected electrons in a specified energy range. The processor also is configured to determine a measurement of the detected electrons in the selected energy range, and to determine an amount of surficial contamination of the optical component with the contaminant substance from the measurement. The overall apparatus can be any of various microlithography apparatus, for example, such as an X-ray microlithography apparatus.

The apparatus can include a projection-optical system, wherein the optical component is in the projection-optical system. In such an instance, the optical component can be, for example, an X-ray-reflective mirror.

The apparatus can include a vacuum chamber enclosing the projection-optical system. In such a configuration, the vacuum chamber typically is connected via an evacuation port to a vacuum pump (which represents a source of contamination to adjacent components). Hence, the optical component desirably would be one that is situated adjacent the evacuation port. Alternatively or in addition, a monitored optical component can be one that is situated in the projection-optical system adjacent a substrate exposed by the X-ray beam. This is because the substrate typically is coated with a resist, which also represents a source of contamination to adjacent optical components.

According to yet another aspect of the invention, methods are provided, in the context of a method for performing microlithography of a substrate with a pattern using an energy beam passing through an optical system, for measuring accumulation of a contaminant substance on a surface of an optical component of the optical system. In an embodiment of such a method, a beam of radiation is directed to impinge on the surface. The radiation is of a quality that causes the surface to emit electrons in response to being irradiated with the radiation. Electrons emitted from the surface are detected. Of the detected electrons, electrons in a specified energy range are selected. The detected electrons in the specified energy range are detected so as to obtain a measurement of a corresponding amount of accumulated contaminant substance on the surface. Hence, it is possible to perform microlithographic exposure while also monitoring the state of contamination of one or more optical components.

The foregoing and additional features and advantages of the invention will be more readily apparent from the following detailed description, which proceeds with reference to the accompanying drawings.

DETAILED DESCRIPTION

The invention is described below in the context of representative embodiments. It will be understood, however, that the invention is not limited to these embodiments.

Representative Embodiment 1

Figure 1:
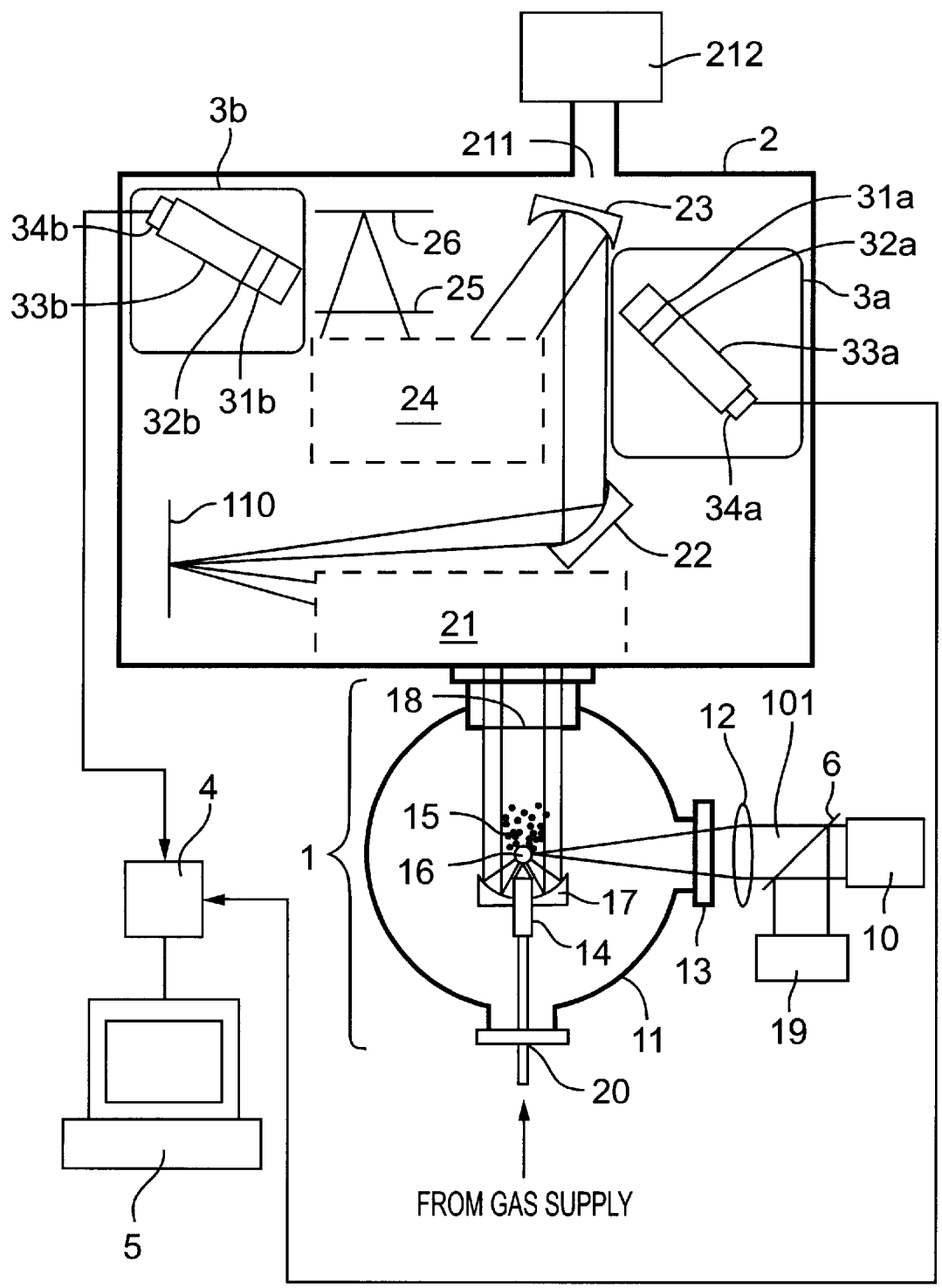
FIG. 1 is a schematic optical diagram of an X-ray microlithography apparatus according to a first representative embodiment of the present invention.

An X-ray microlithography apparatus according to this embodiment is shown in FIG. 1. The FIG.-1 embodiment performs projection-exposure using a step-and-scan mode of operation, and utilizes "soft" X-rays as an illumination light for exposure. The FIG.-1 apparatus comprises, inter alia, a light-source system 1 that produces a beam of soft X-rays, an exposure system 2 that irradiates a reflective reticle with the X-ray beam and projects an image of the reticle onto a substrate (wafer), and a detection system (comprising detectors 3a, 3b) that measures the state of contamination of certain respective adjacent components of the exposure system 2.

In this embodiment, the light-source system 1 is a laser-plasma X-ray (LPX) source, comprising a laser 10, a beamsplitter 6, a lens 12 that focuses the light emitted from the laser 10, and a vacuum chamber 11. The laser 10 produces a pulsed laser beam 101. The vacuum chamber 11 comprises a window 13 transmissive to the laser beam 101, a nozzle 14 that introduces a gas of a target substance into the vacuum chamber 11, a parabolic mirror 17 that reflects emitted X-rays in a specified direction, and a window 18 through which X-rays pass out of the vacuum chamber 11.

The pulsed laser light 101 emitted from the laser 10 passes through the beamsplitter 6 and is refracted by the lens 12. The refracted laser light passes through the window 13 and is focused at a point inside the vacuum chamber 11.

Meanwhile, a suitable gas (e.g., xenon) constituting a "target substance" passes from a supply through a feed-through 20 into the vacuum chamber 11. The gas is discharged into the vacuum chamber 11 through the nozzle 14. The nozzle 14 desirably is configured as a pulsed-jet nozzle to introduce the target gas as discrete jet pulses into the vacuum chamber 11. To such end, the nozzle 14 is configured to turn on and off very accurately to produce, for example, discrete 500-microsecond pulses of the target gas. The nozzle 14 also desirably operates with a substantial back-pressure (e.g., 50 atmospheres) to better define the pulses of target gas.

Each pulse of target gas jetting into the vacuum chamber 11 from the nozzle 14 exhibits an abrupt drop in temperature due to adiabatic free expansion. This temperature drop causes atoms of the target gas to adhere to each other due to van der Waals forces, causing formation of clusters 15 of the target gas each containing several tens to several tens of thousands of atoms of the target gas. Whenever a cluster 15 is irradiated with a pulse of laser light 101 (as focused by the lens 12), a plasma 16 is produced. In actual practice, each cluster 15 encounters a pulse of the laser light 101 several hundred microseconds after discharge of the pulse of target gas from the nozzle 14.

The plasma 16 produces X-rays that radiate away from the cluster. The X-rays, thus emitted in pulsatile form, reflect from the parabolic mirror 17, which is situated in the vicinity of the nozzle 14 to ensure that the X-ray pulses propagate in a specified direction away from the mirror 17. To reflect X-rays, the mirror 17 comprises a multi-layer surficial film. The 3-D profile of the mirror 17 is generated by rotating a parabola. The mirror 17 is positioned such that X-rays reflected from it propagate as essentially parallel rays.

The X-rays reflected from the mirror 17 pass through the window 18. The window 18 includes an X-ray filter to block visible light so that only X-rays pass through the window 18. The X-rays then enter another vacuum chamber housing the exposure system 2.

The intensity of the X-rays produced by the light-source system 1 varies according to the energy of the pulsed laser beam 101. To monitor the beam energy, a portion of the beam 101 is split off by the beamsplitter 6 and directed to a light detector monitor 19 that continuously monitors the beam. Thus, the intensity of the X-rays is estimated by monitoring the energy per pulse of the laser light produced by the laser 10, or by determining a mean energy produced by a defined number of laser pulses.

The exposure system 2 comprises an illumination-optical system 21; mirrors 22, 23 that form a first projection-optical system; a second projection-optical system 24, and a filter 25. The exposure system 2 utilizes a reflective reticle 110 that defines the circuit pattern to be projected, and a substrate 26 to which the reticle pattern is "transferred."

Figure 2:
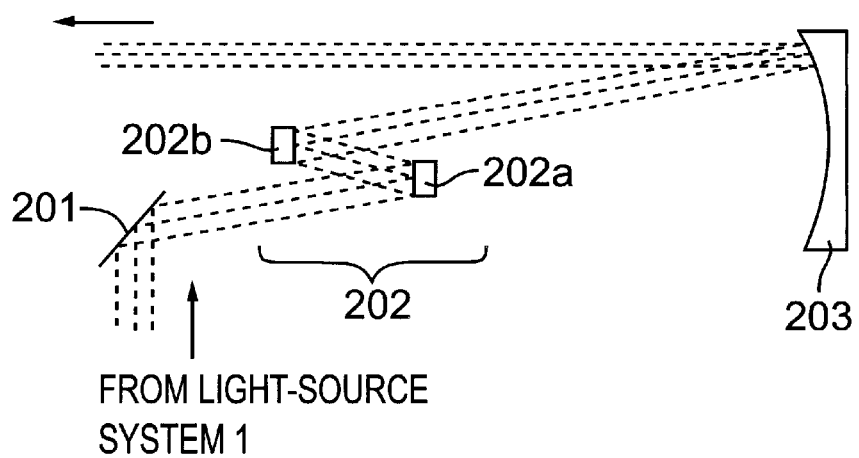
FIG. 2 is a schematic optical diagram of the illumination-optical system of the FIG.-1 embodiment.

The X-rays produced by the light-source system 1 first enter the illumination-optical system 21, of which certain details are shown in FIG. 2. The illumination-optical system 21 comprises a mirror 201, a first reflective-element group 202a, a second reflective-element group 202b, and a condenser mirror 203. The first and second reflective-element groups 202a, 202b collectively constitute a reflective-type fly-eye optical system 202, as disclosed in Japanese Kôkai (laid-open) Patent Application No. 10-47400.

The essentially collimated beam of X-ray pulses reflected from the parabolic mirror 17 of the light-source system 1 is reflected by the mirror 201. The reflected rays propagate to the first reflective-element group 202a. The first reflective-element group 202a comprises an array of multiple reflective surfaces (i.e., a plurality of small mirror elements). From the first reflective-element group 202a, the rays propagate to the second reflective-element group 202b that comprises an array of reflective surfaces that differ from the respective reflective surfaces of the first reflective-element group 202a.

In the reflective type fly-eye optical system 202, the first reflective-element group 202a subjects the X-rays from the light-source system 1 to wavefront division to produce a plurality of light-source images downstream of the first reflective-element group 202a. The second reflective-element group 202b is situated at or near where the plurality of light-source images are formed. The individual reflective surfaces (one for each respective wavefront) of the second reflective-element group 202b reflects the X-rays toward the condenser mirror 203. Hence, the second reflective-element group 202b also functions as a field mirror directing the plurality of light-source images to the condenser mirror 203. The focal position of the condenser mirror 203 is situated in the vicinity of the position where light-source images are formed by the first reflective-element group 202a. X-rays reflected from the condenser mirror 203 propagate to the reticle 110 to illuminate a specified region on the reticle 110 uniformly. I.e., the individual light-source images desirably illuminate the specified region on the reticle 110 in an overlapping manner (due to the action of the fly-eye optical system) to illuminate the region uniformly.

Figure 3:
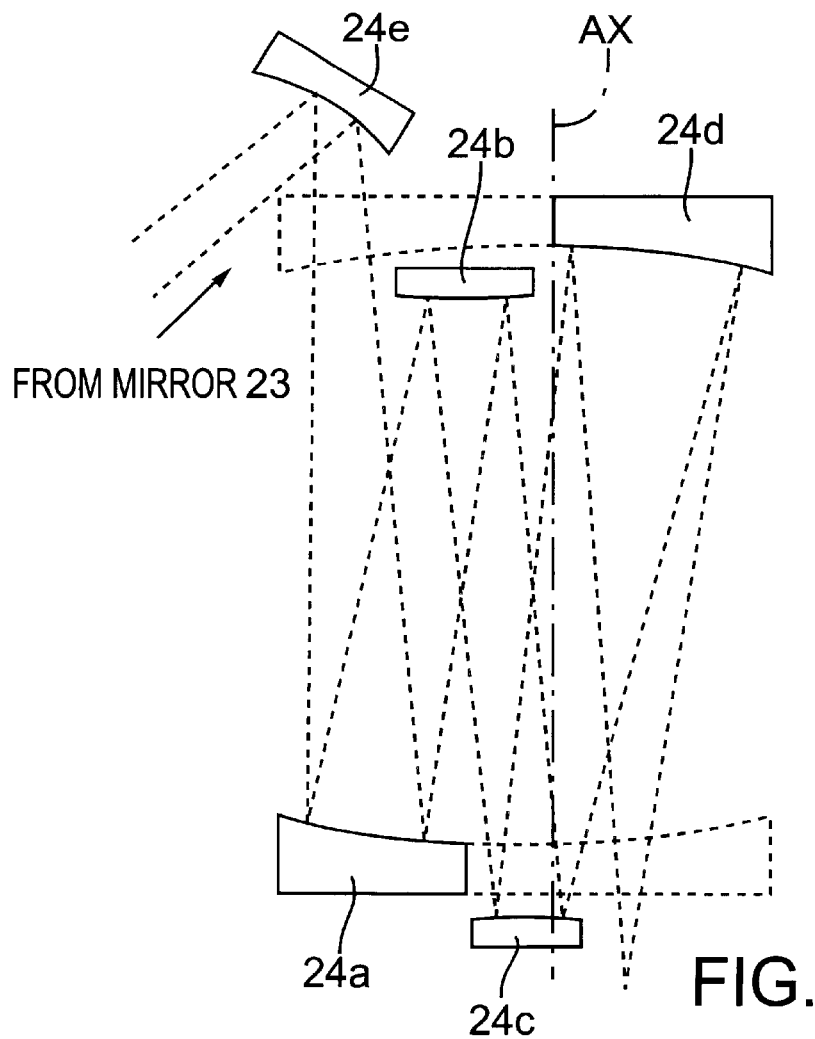
FIG. 3 is a schematic optical diagram of the second projection-optical system of the FIG.-1 embodiment.

X-rays reflected by the reticle 110 are reflected by the mirrors 22, 23 (collectively constituting the first projection-optical system) and then enter the second projection-optical system 24. The second projection-optical system 24, as shown in FIG. 3, comprises multiple reflective mirrors 24a–24e. The first mirror 24a has a concave profile; the second mirror 24b has a convex profile; the third mirror 24c has a convex profile; and the fourth mirror 24d has a concave profile. The fifth mirror 24e has a concave profile and is used to conduct the X-rays reflected by the mirror 23 to the first mirror 24a. The first mirror 24a and second mirror 24d are situated and oriented so that their respective optical axes are coincident at a common axis AX. The first mirror 24a, second mirror 24b, and fourth mirror 24d define respective cut-outs so as not to block the light path collectively defined by the mirrors 24a–24d.

The X-rays reflected by the reticle 110 are formed by the second projection-optical system 24 into a "reduced" (demagnified) image of the reticle pattern on the substrate 26. The image is smaller than the reticle pattern by a specified demagnification ratio β (e.g., |β|=¼, ⅕, or ⅙).

Although not shown in FIG. 1, the reticle 110 is mounted to and supported by a reticle stage that is movable in at least one dimension. Similarly, the substrate 26 is mounted to and supported by a substrate stage that desirably is movable in three dimensions. During scanning exposure of the substrate 26, the substrate stage is moved in a specified direction and at a specified velocity dictated by the demagnification ratio of the second projection-optical system 24. Meanwhile, the reticle stage is moved in a specified direction and velocity. By such coordinated movements, the reticle pattern is scanned and exposed within specified "shot" regions on the surface of the substrate 26.

Each of the reflective mirrors discussed above comprises a surficial multi-layer film for reflecting X-rays. Desirably, the multi-layer film consists of alternating layers of molybdenum and silicon. The period of the layers of the film is set so that the peak wavelength of the reflected X-rays is 13.5 nm. The reticle 110 is constructed similarly.

The vacuum chamber enclosing the exposure system 2 includes an evacuation port 211 through which the atmosphere inside the chamber is evacuated. To such end, the evacuation port 211 is connected to a vacuum pump 212. During operation, the vacuum chamber is maintained at a subatmospheric pressure.

The detectors 3a, 3b are used for measuring the state of contamination of respective adjacent optical components of the exposure system 2. The detectors 3a, 3b are located inside the vacuum chamber enclosing the exposure system 2, and are situated in the vicinity of the optical elements that most likely are to be contaminated during use.

Impingement of X-rays on the surface of an optical component tends to cause emission of photoelectrons from the surface of the optical component. (A similar phenomenon occurs when surfaces of certain materials are irradiated with other types of electromagnetic radiation, such as ultraviolet radiation, or electrons.) If the incident X-rays are sufficiently monochromatic, then the energy of photoelectrons emitted from the surface of the optical component is determined by the energy of the incident X-rays and on the material constituting the surface of the optical component. Specifically, where $E_x$ is the photon energy of the X-rays, and $E_b$ is the bond energy of the material constituting the surface of the optical component, the energy $E_p$ of emitted photoelectrons is equal to the difference $E_x-E_b$ (ignoring the work function). The energy range of the photoelectrons is substantially the same as the energy range of the X-rays.

Figure 4:
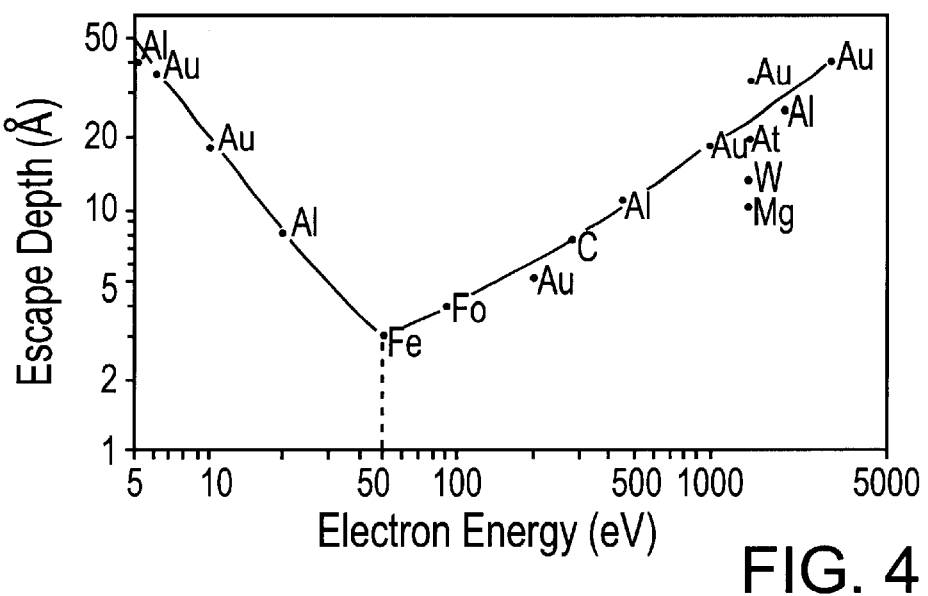
FIG. 4 is a graph showing the correlation between the escape depth of photoelectrons or Auger electrons from a substance and the energy of these electrons (from Hüfner, *Photoelectron Spectroscopy*, Springer Verlag, 1995, p. 8).

The "escape depth" is the average depthwise distance (from the surface of a substance) within which photoelectrons can escape from the surface of the substance without undergoing inelastic scattering. The escape depth depends on the energy of the photoelectrons. FIG. 4 shows the relationship between escape depth and photoelectron energy. The abscissa (horizontal axis) of FIG. 4 is photoelectron energy, and the ordinate (vertical axis) is escape depth.

As is evident in FIG. 4, the escape depth ranges from several Ångstroms to several tens of Ångstroms whenever the energy range of the photoelectrons is several tens of eV to 1 KeV. Such an escape depth is extremely shallow. Under such conditions, a deposit of a contaminant substance (even an extremely thin deposit) on the surface of an optical component will reduce or prevent the emission of photoelectrons from the material constituting the optical component. An apparatus according to this embodiment exploits this phenomenon to provide monitoring of contaminant deposition on certain optical components.

For example, an apparatus according to this embodiment can be used for monitoring, in an X-ray microlithography apparatus, (1) surface contamination of certain optical components by detecting photoelectrons emitted from the optical-component surfaces whenever the surfaces are irradiated by X-rays, (2) selecting data relating to the photoelectrons emitted from the surfaces so as to distinguish whether and to what extent the surfaces have become contaminated, and (3) monitoring the quantity of photoelectrons produced over time to ascertain the rate of contamination. More specifically, the surfaces of the optical components are irradiated with X-rays so as to produce photoelectrons having an energy of several tens of eV to about 1 KeV (which is the usual range of bond energy of substances normally used to form the surficial layers on an X-ray optical component). The emitted photoelectrons are selected on the basis of energy so as to allow detection of photoelectrons in a specified energy range. Thus, photoelectrons can be selected that are emitted from the actual substance constituting the top-most layer. The selected photoelectrons are quantified. If the number of selected and detected photoelectrons exhibits a decline over time, then it can be inferred that contaminant molecules have become adhered to the irradiated surface. By comparing the detected number of photoelectrons with a threshold value, a determination can be made of whether to clean or replace the subject optical component.

It will be understood that the detected electrons are not limited to photoelectrons. The state of surficial contamination also can be determined by measuring Auger electrons emitted from an irradiated surface. Auger electrons can be produced whenever a material is irradiated with energetic radiation such as an electron beam, a beam of ultraviolet light, or a beam of X-rays. For example, whenever a material is irradiated by X-rays, an X-ray quantum can strike an electron in an atom of the surface material. If the struck electron is emitted as a photoelectron, a "hole" or vacancy is left. It is energetically favorable for an electron from an adjacent level to shift to and recombine with the hole where the recombining electron experiences a drop in energy. The excess energy and momentum of the recombining electron and hole are shifted to an "Auger electron" emitted from the material. In a vacuum, the Auger electron has an energy $E_a$ obtained by subtracting a sum $(E_1+E_2)$ from the bond energy $E_b$ of the photoelectron, wherein $E_1$ is the energy of the electron filling the hole and $E_2$ is the bond energy of the electron emitted as an Auger electron. I.e., $E_a=E_b-(E_1+E_2)$.

As with photoelectrons, Auger electrons can have an energy within a range of several tens of eV to approximately 1 KeV. Accordingly, as with photoelectrons, the escape depth of Auger electrons is extremely shallow. Hence, as with photoelectrons, the state of contamination of an optical component can be detected by selecting and quantifying Auger electrons emitted from the surface of the optical component. (Auger electrons have a particular energy regardless of the wavelength of an incident X-ray and the energy of incident electrons. Because a database of energy of Auger electrons already exists for each chemical element, Auger electrons can be distinguished from photoelectrons.)

Thus, the detectors 3a, 3b detect photoelectrons or Auger electrons, within a specified energy range, produced by a respective adjacent optical component 23, 25. The specified energy range typically is a portion of the overall energy range of photoelectrons or Auger electrons emitted from the respective optical component. From the resulting data, the detectors 3a, 3b can determine the state of contamination of the respective optical components.

To perform detections in the manner summarized above, the detector 3a, 3b desirably is configured as a "time-of-flight" (TOF)-type analyzer. A typical TOF-type analyzer comprises a magnetically shielded flight tube 33a, 33b and a micro-channel plate 34a, 34b for detecting photoelectrons or Auger electrons. Each flight tube 33a, 33b includes mesh electrodes 31a, 31b and 32a, 32b, respectively, which are used to apply an inhibiting electric field to the photoelectrons or Auger electrons (to lower their energy) propagating through the respective flight tube. As an analysis technique, TOF is well suited for use in situations involving a pulsed light source (such as the laser 10). Also, because TOF exhibits a higher electron-detection efficiency than other analysis techniques, electrons are detected with good sensitivity.

In the TOF technique, whenever an object being tested is irradiated with X-rays from a pulsed X-ray source for a very short period of time (e.g., a few nanoseconds or less), photoelectrons are emitted more or less simultaneously from an irradiated object (within the same time period as the corresponding pulse of X-rays impinging on the object). The emitted electrons collectively have a range of energies; electrons having relatively high energy have a correspondingly higher velocity than lower-energy electrons. Hence, the higher-energy electrons reach the detectors 3a, 3b quickly, and the lower-energy electrons reach the detectors 3a, 3b more slowly.

More specifically, the relationship of the energy (E) of an emitted electron, the mass (m) of the electron, the distance (L) from the irradiated object to the detector, and the time (T) required by the electron to reach a detector is expressed by the following:

$$E = \frac{1}{2}mv^2 = \frac{m}{2}\left(\frac{L}{T}\right)^2 \quad (1)$$

Accordingly, if the distance L to a detector 3a, 3b is known, then the energy of the emitted electrons can be ascertained by measuring the time of flight T of the electrons.

The energy resolution obtained in TOF-type analysis is given by Equation (2):

$$|\delta E| = \frac{mL^2}{T^3}\delta T = \frac{2E}{T}\delta T \quad (2)$$

Here, δT is the temporal width of the system, which includes the temporal pulse width of the X-rays, the response time of the detector, etc. If δT is fixed, then energy resolution is improved with increasing time of flight T. Accordingly, in the detectors 3a, 3b used in this embodiment, energy resolution is improved by applying an inhibiting electric field to lower the energy E of electrons entering the detectors. Lowering the electron energy correspondingly prolongs the time of flight T. Increasing the energy resolution allows finer energy spectra to be detected.

In the FIG.-1 configuration, the detectors 3a, 3b monitor the state of contamination of the mirror 23 and filter 25, respectively. The mirror 23 is situated nearest the vacuum pump 212 of all components in the exposure system 2, and thus is most vulnerable to contamination by pump oil. Similarly, the filter 25 is situated nearest the substrate 26 of all components in the exposure system 2, and thus is most susceptible to contamination by molecules of resist released from the surface of the substrate 26 during microlithographic exposure. Accordingly, the detectors 3a, 3b monitor respective components that are most susceptible to contamination.

In each detector 3a, 3b, an appropriate respective voltage is applied between the mesh electrodes 31a and 32a, and between the mesh electrodes 31b and 32b, respectively. Passage of electrons through the mesh electrodes reduces the energy of electrons emitted from the mirror 23 and filter 25, respectively. The electrons then complete their journey through the respective flight tube 33a, 33b and impinge on the respective micro-channel plate 34a, 34b. The micro-channel plates 34a, 34b produce respective output signals that are routed outside the exposure system 2 via a respective coaxial cable to a processor 4.

Figure 5:
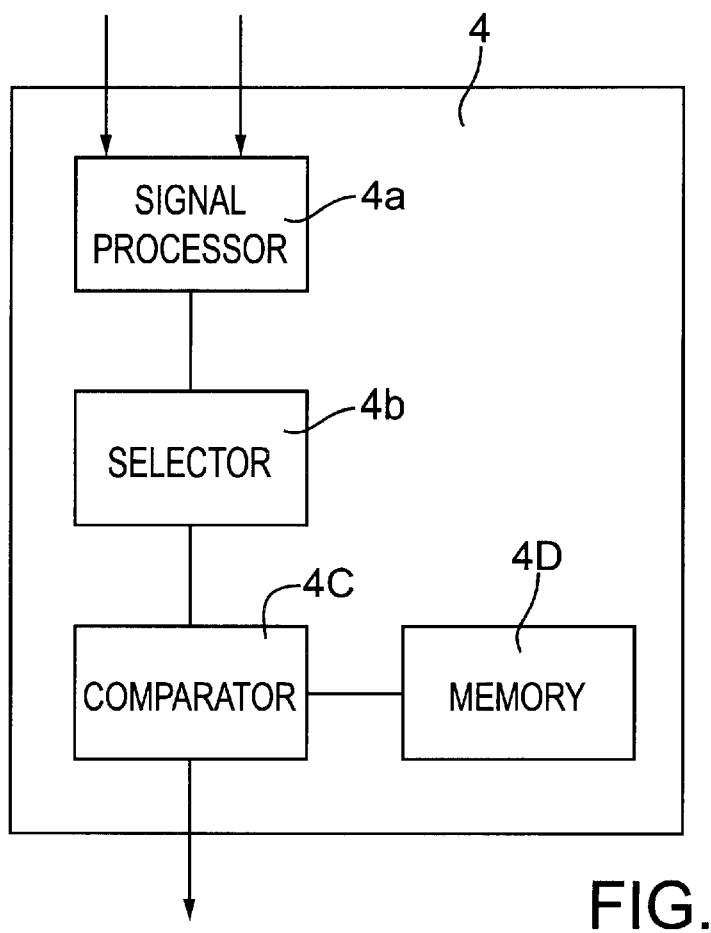
FIG. 5 is a block diagram of the processor of the FIG.-1 embodiment.

The processor 4 receives data relating to the numbers of electrons detected by the respective micro-channel plates 34a, 34b. The respective states of contamination of the mirror 23 and filter 25 are detected by measuring the respective numbers of electrons within certain respective energy ranges and comparing the measured numbers to respective threshold values. To such end, the processor 4 includes a signal processor 4a, a selector 4b, a comparator 4c, and a memory 4d, as shown in FIG. 5.

The signal processor 4a receives the output signals from the micro-channel plates 34a, 34b, and produces corresponding digital signals within respective energy ranges. The signal processor 4a also can be configured to convert the output signals from the micro-channel plates into respective electron spectra. Since there is a direct correspondence between electron energy and an electron's time of flight, as described above, the signal processor 4a can be configured to produce data for electrons within a pre-selected TOF window.

The selector 4b determines the respective energy ranges or TOF ranges within which data regarding electrons emitted from the surface of the target component are to be processed. Such a determination normally is made beforehand from the frequency of X-rays emitted from the light-source system 1 and from the respective substance on the surface of the filter 25 and mirror 23. In the data output from the signal processor 4a, the selector 4b selects, for downstream processing, data corresponding to electrons in the pre-selected range. The selector 4b outputs data indicating the number of detected electrons within the respective pre-selected range. The output data are routed to the comparator 4c.

In the comparator 4c, the quantity of electrons in the pre-selected energy or TOF range, or in data provided by the selector 4b, are compared to respective threshold values. If the quantity of detected electrons is smaller than the respective threshold value, then the mirror 23 or filter 25 is deemed to be contaminated and requiring replacement or cleaning. Such information can be displayed on a display 5.

The memory 4d stores data concerning specified threshold values used by the comparator 4c. Each threshold value corresponds to a respective quantity of electrons that would be produced by the surface of the respective optical component (e.g., mirror 23 or filter 25) at an excessive level of contamination (requiring replacement or cleaning of the component). Such data can be input into the memory 4d beforehand by the user.

It will be understood that the data processing, summarized above, performed by the processor 4 (with portions 4a–4d) could be performed with equal facility by a computer or other CPU.

In the foregoing description, the key data for comparison purposes is number of electrons. It will be understood that, in lieu of number of electrons, comparisons can be made of any data having a correlation with number of electrons, such as output signals directly from a micro-channel plate.

In mirrors used in conventional X-ray microlithography apparatus, silicon normally is used as the outermost layer in order to prevent changes in reflectivity caused by surficial oxidation of molybdenum. However, the 2p bond energy of silicon is 99 eV, and the photon energy of 13.5-nm X-rays is 91 eV. Under such conditions, impingement of X-rays on the mirror 23 would not produce any emitted electrons. Accordingly, the mirror 23 of this embodiment desirably includes, as an outermost layer, a layer of platinum. To minimize absorption of incident X-rays while producing a sufficient number of electrons, the thickness of the platinum layer is no greater than several Angstroms. (For example, a platinum layer having a thickness of approximately 5 Angstroms exhibits a drop in reflectivity of 5%, which can be ignored in practical terms. Furthermore, when platinum is irradiated with 13.5-nm X-rays, the bond energy of electrons of the 4f level is 74.5 eV (4f5/2) and 71.2 eV (4f7/2). From such a mirror, the emitted photoelectrons have energies of approximately 16.5 eV and 19.8 eV, respectively.

X-rays emitted from the plasma 16 generally have a broad range of wavelengths. However, when such X-rays are reflected by a multi-layer-film surface such as the parabolic mirror 17, mirrors of the illumination-optical system 21, the reflection reticle 110, and mirror 22, the spectral width ($\delta\lambda$) of the X-rays is narrowed. I.e., the spectral width $\delta\lambda$ is limited by the bandwidth of the multi-layer films, so that the spectral width of the X-rays incident on the mirror 23 has a bandwidth of $\delta\lambda/\lambda$=approximately 2.5% (where $\lambda$ is the wavelength of the incident X-ray). Since the X-ray wavelength in this embodiment is 13.5 nm, the spectral width $\delta\lambda$ is 0.34 nm. Hence, $\delta E$=2.3 eV in terms of photon energy. Therefore, photoelectrons having a spectral energy width of approximately 2.3 eV, centered on 16.5 eV and 19.8 eV, respectively, are produced from the platinum layers on the respective mirrors 23, 25.

Accordingly, among the electrons from the mirrors 23, 25 detected by the detectors 3a, 3b, the electrons that are quantified are those having an energy within a 2.3-eV window centered on 16.5 eV and on 19.8 eV, respectively. The quantification is performed, as discussed above, by the processor 4. Whenever the quantity of electrons is smaller than the threshold value, the need for measures such as replacement or cleaning of the respective optical component is indicated to the user.

Therefore, in this embodiment, if electrons cannot be produced (at the particular wavelength of X-ray being used) from an X-ray-reflective optical component that is being monitored, then at least a portion of the surface of the optical component is coated with a substance that will produce electrons. The coating substance is different from the substances used to make the surface reflective to X-rays. The relative area of the surface that is coated must be sufficient to produce a usable number of electrons.

The coating substance is not limited to platinum. Any of various substances can be used so long as the selected substance emits inner-shell electrons when irradiated by electromagnetic radiation at the particular wavelength used.

Furthermore, the coating substance desirably is a material having an appropriate escape depth of photoelectrons. As seen in FIG. 4, whenever the emitted electrons from an optical component have an energy of approximately 10 eV or less, or an energy of several hundred eV or greater, the escape depth is relatively deep, i.e., several tens of Angstroms. But, in the range from approximately 30 eV to 100 eV, the escape depth is only a few Angstroms. Utilizing the electron-energy dependence of this escape depth, it is desirable that the coating substance absorb X-rays, thus causing the emitted energy to have an appropriate value.

Furthermore, in the detectors 3a and 3b in this embodiment, if the number of detected electrons is insufficient, then an electrostatic lens or magnetic lens (e.g., magnetic bottle, etc.) can be used to capture electrons over a wider angle.

The detector 3b is situated relative to the filter 25 in this embodiment. But, if the filter 25 is not used in the system, then the detector 3b can be situated relative to a mirror near the resist.

Representative Embodiment 2

An X-ray microlithography apparatus according to this embodiment differs from Representative Embodiment 1 only in the processor 4. Components in this embodiment that are identical to respective components in Representative Embodiment 1 have the same respective reference numerals and are not described further. This embodiment can be understood by reference to FIG. 5.

In this embodiment, contamination of selected optical components is monitored by selecting electrons (among the electrons detected by the micro-channel plates 34a, 34b) emitted from contaminant substances predicted to adhere to the optical components. With increases in the contaminant load on an optical component, the relative quantity of electrons emitted from the contaminant substance on the component increases until the contaminant film reaches a specified thickness.

The processor 4 in this embodiment reviews the output signals produced by the micro-channel plates 34a, 34b and selects signals produced by electrons emitted by the contaminant substances. The signals are selected based on the predicted contaminant substances and the energy of the X-rays radiated by the light-source system 1. Thus, with respect to the processor 4 in this embodiment, only the selector 4b and comparator 4c differ from corresponding components in Representative Embodiment 1.

The selector 4b selects signals, in the output of the signal processor 4a, corresponding to a electrons within a predetermined energy window expected to be emitted from contaminant substances on the optical components 23, 25. The energy range spanned by the window is determined based on the predicted contaminant substances and the energy of X-rays produced by the light-source system 1. The selector 4b outputs data, concerning the number of electrons within the selected range, to the comparator 4c.

In the comparator 4c, the number of electrons detected in the preselected energy range is compared with a pre-stored threshold value.

If the number of detected electrons is greater than the threshold value, then it is inferred that the mirror 23 and/or filter 25 requires replacement or cleaning. This information is displayed by the display 5.

The threshold value stored in the memory 4d is the same as a value representing the quantity of electrons expected to be produced from the contaminant substances if the mirror 23 or filter 25 were in a contaminated state requiring replacement or cleaning.

Until the thickness of contaminant accumulation on the mirror 23 or filter 25 reaches approximately the escape depth of the electrons, the number of electrons in the selected energy range is roughly proportional to the amount of contaminant substance that has accumulated on the optical component. Accordingly, the amount of accumulated contaminant substance also can be measured by detecting the number of electrons emitted from the contaminant substance, as described above.

Representative Embodiment 3

An X-ray microlithography apparatus according to this embodiment differs from Representative Embodiment 1 only in the processor 4. Components in this embodiment that are identical to respective components in Representative Embodiment 1 have the same respective reference numerals and are not described further. This embodiment can be understood by reference to FIG. 5.

In this embodiment, among the electrons detected by the micro-channel plates 34a, 34b, electrons emitted from the substance forming the outermost surface layer of the mirror 23 or filter 25 and electrons emitted from any of various contaminant substances predicted to adhere to these optical components are selected. The state of contamination of the optical components is detected by comparing the respective numbers of electrons. More specifically, the selector 4b selects, from the data output from the signal processor 4a, only data relating to the number of electrons emitted from the substance forming the outermost surface layer of the mirror 23 or filter 25 and data relating to the number of electrons emitted from candidate contaminant substances. The selected data are output to the comparator 4c.

In the comparator 4c, for each component 23, 25, the ratio of the number of electrons emitted from the accumulated contaminant to the number of electrons emitted from the substance forming the outermost surface layer of the component is determined. The need to replace or clean the component is judged on the basis of whether or not the ratio exceeds a threshold value.

Representative Embodiment 4

An X-ray microlithography apparatus according to this embodiment differs from Representative Embodiment 1 in that the processor 4 of Representative Embodiment 1 is replaced in this embodiment with a substance-identifier. All components of this embodiment that are similar to respective components of Representative Embodiment 1 have the same reference numerals and are not described further.

More specifically, in this embodiment, a spectrum of the electrons emitted from the mirror 23 or filter 25 is obtained from the signals output from the micro-channel plates 34a and 34b, respectively. Contaminant substances are identified from values of peak electron energies occurring within the spectrum.

As described above, the energy of emitted photoelectrons or Auger electrons is determined by the frequency of light (e.g., X-rays) irradiated from the light-source system 1 and by the substance actually irradiated by the light. Accordingly, the generating source of the emitted photoelectrons or Auger electrons can be identified from the respective locations and magnitudes of peaks exhibited in the obtained electron spectrum.

Accordingly, this embodiment comprises a substance-identifier instead of a processor 4. The substance identifier comprises a component similar to the signal processor 4a of Representative Embodiment 1 and includes a database of chemical elements and a data processor. The substance identifier acquires data relating to the energy spectrum of electrons detected by the micro-channel plates 34a, 34b. The substance identifier detects peak values in the obtained electron-spectral data and identifies the particular substance that emitted the electrons having the peak values. For comparison purposes, peak profiles are stored in advance for various candidate contaminant compounds.

In addition to a substance identifier, this embodiment can include a processor 4 as in Representative Embodiment 1. With such a configuration, this embodiment not only identifies the specific contaminants adhering to the target optical components, but also determines the extent of contamination.

Representative Embodiment 5

Figure 6:
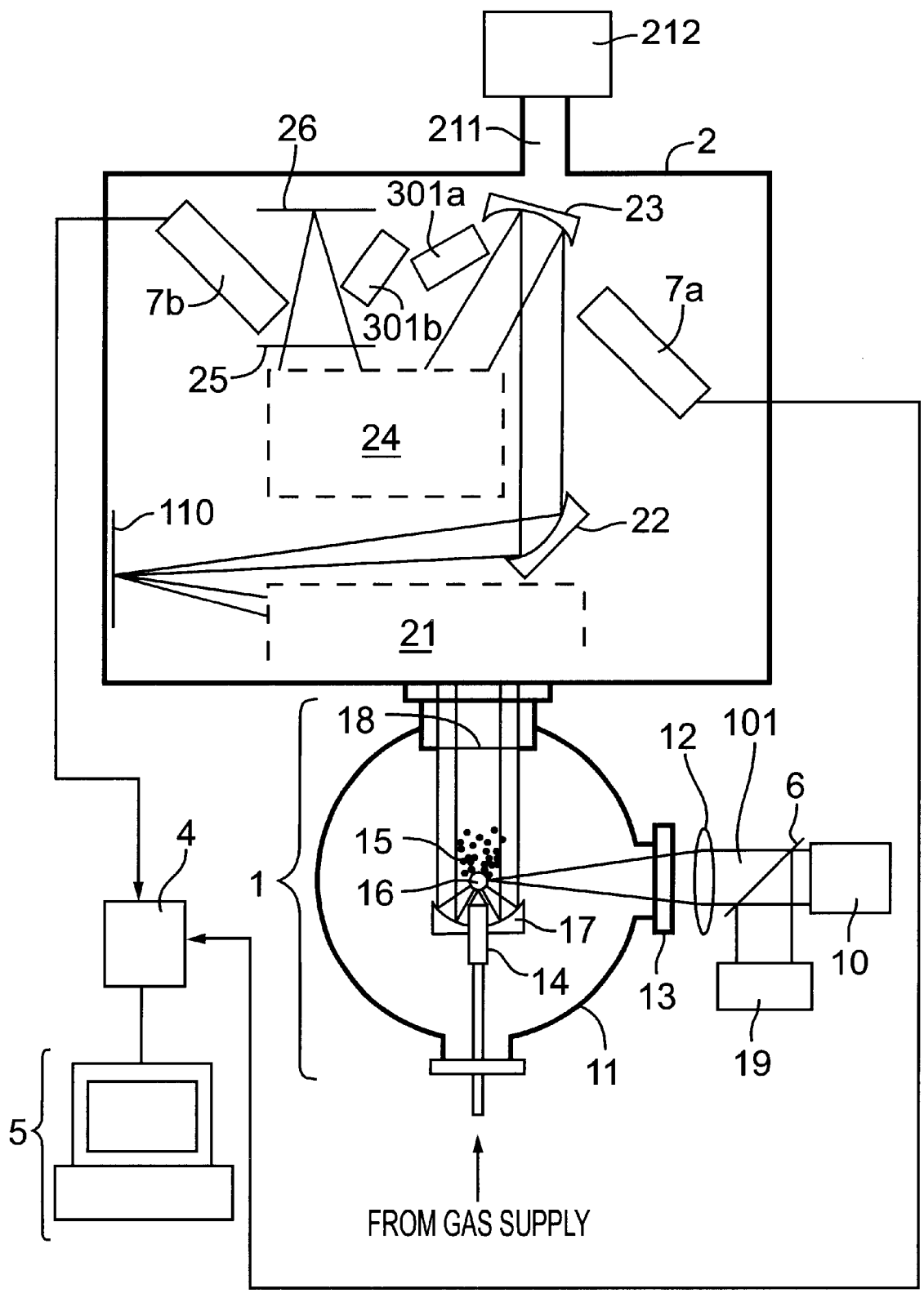
FIG. 6 is a schematic optical diagram of an X-ray microlithography apparatus according to a fifth representative embodiment of the invention.

An X-ray microlithography apparatus according to this embodiment is shown in FIG. 6. Components in FIG. 6 that are similar to corresponding components in Representative Embodiment 1 have the same reference numerals and are not described further.

The FIG.-6 configuration comprises electron-energy analyzers 7a, 7b instead of the detection systems 3a, 3b, respectively, for detecting electrons emitted from the mirror 23 and filter 25, respectively. The electron-energy analyzers 7a, 7b are mounted in a manner allowing the analyzers 7a, 7b to be oriented at a desired angle relative to the mirror 23 and filter 25.

More specifically, the electron-energy analyzers 7a, 7b, have a cylindrical configuration, and have specific angular ranges (relative to the cylindrical axis) of detection. The detection direction can be varied by varying the angle of a respective cylindrical axis of an energy analyzer 7a, 7b. Adjusting the detection direction allows adjustment of the detectable depth at which emitted electrons are generated. This angular dependence (relative to the surface of the respective optical component) of the detectable depth of emitted electrons is shown in FIGS. 7(a)–7(b).

Figure 7A:
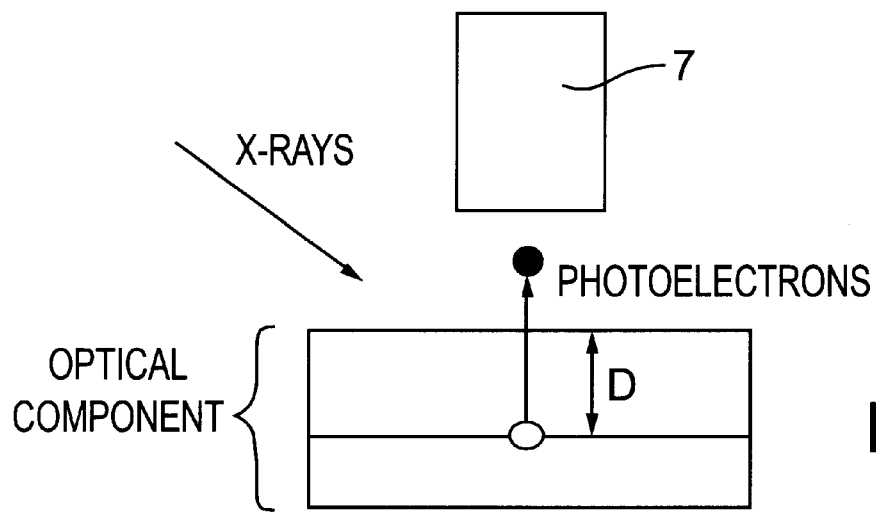
FIGS. 7(a)–7(b) schematically depict the relationship between the angle of an energy detector relative to the surface of an optical component and the detectable depth of emitted electrons from the optical component as detected by the energy detector.

FIG. 7(a) shows a situation in which an energy analyzer 7 is oriented normal to the surface of a respective optical component. In this configuration, emitted electrons are detectable within a region extending to a depth of d from the surface when the optical component is irradiated with X-rays.

Figure 7B:
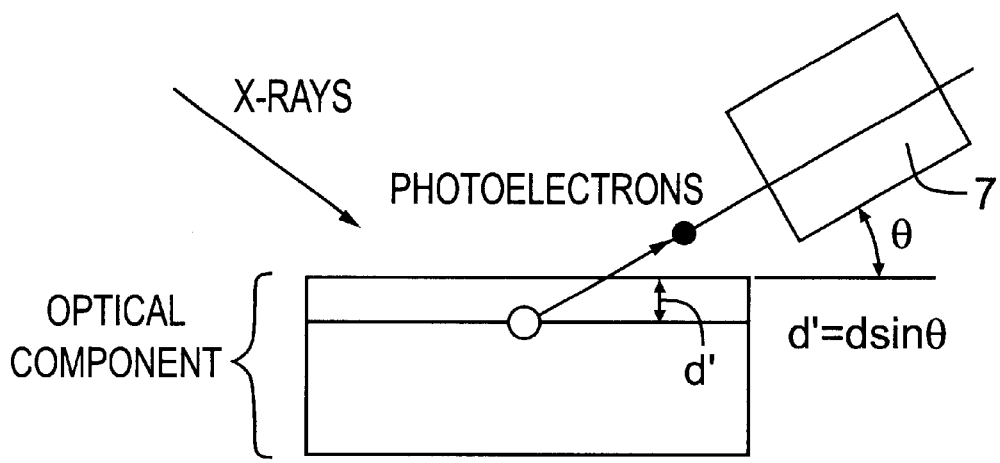

FIG. 7(b) shows a situation in which an energy analyzer 7 is oriented at a small angle $\theta$ (compared to FIG. 7(a)) from the surface of the respective optical component. In this configuration, the energy analyzer 7 only can detect emitted electrons to a depth of $d\sin\theta$ from the surface of the respective optical component. In both configurations (FIGS. 7(a) and 7(b)), the distance traveled by the electrons through the optical component corresponds to the deepest detectable position in the component. The deepest detectable position is a function of electron escape depth, described above.

By orienting the energy analyzers 7a, 7b such that their respective detection angles are shallow relative to the surface of the corresponding optical component, the energy analyzers 7a, 7b are made extremely sensitive to the conditions on the surface of the respective optical component. As a result, only electrons emitted from a shallow region below the surface of the respective optical component are detected.

In a case in which absorption of X-rays by the contaminant substances is small (such that absorption of X-rays is not a problem unless the contaminant substances adhere somewhat thickly to the target optical components), it is desirable to install the energy analyzers 7a, 7b in a more normal orientation to the respective optical components. In any event, the angles of the energy analyzers 7a, 7b desirably are adjustable so that emitted electrons can be detected to a desired depth. This configuration (in which the orientation of a detector can be changed relative to its respective optical component) can be applied with equal facility to other embodiments of the invention.

Referring further to FIG. 6, this embodiment also comprises light sources 301a, 301b for use during inspections. The light sources 301a, 301b are situated and configured to irradiate the mirror 23 and filter 25, respectively, with high-intensity X-rays so that photoelectrons or Auger electrons from the mirror 23 and filter 25, respectively, can be detected in sufficient quantities. Each of the inspection light sources 301a, 301b desirably comprises an individual X-ray tube with aluminum electrodes to produce X-rays of the Kα line of aluminum. The Kα line has a high photon energy and is capable of exciting and causing emission of inner-shell electrons of almost all substances.

During operation of an X-ray microlithography apparatus according to any of the foregoing representative embodiments, if for example the mirror 23 is freshly cleaned or new, then only the electron spectrum of the surficial layer (e.g., silicon or platinum) is produced. As the apparatus is used, contaminant(s) (e.g., oil from the vacuum pump 212) are deposited on the mirror 23. The gradual accumulation of such a deposit causes the optical performance of the mirror 23 (e.g., reflectivity or transmissivity) to deteriorate gradually. However, the deposits cause the appearance of the distinct electron spectrum of carbon- and oxygen-containing components of the oil adhering to the mirror 23. The amount of contaminant(s) adhering to the mirror 23 is ascertained from the intensity of the distinct photoelectron spectra. From data concerning the amounts, whether or not to clean or replace the mirror 23 can be determined.

Apparatus according to the invention are not limited to apparatus 10 that include a source of X-rays. The subject apparatus can include apparatus having no X-ray source.

Furthermore, the "light" source used to make determinations of contaminants of optical components is not limited to an X-ray source.

Any light source can be used with which it is possible to obtain emission of electrons whenever a target optical element and/or contaminant substance is irradiated by the source. For example, irradiation alternatively can be performed using an electron beam or ultraviolet light beam. If an ultraviolet light source is used, then the light source desirably emits light having a line spectrum.

The electrons excited by being irradiated are not limited to inner-shell electrons. Outer-shell electrons also may be excited and emitted, and counted.

If the "light" source 10 is not pulsed, then detectors 3a, 3b other than those described in Representative Embodiment 1 can be used, such as an electrostatic concentric-hemispherical analyzer or cylindrical-mirror analyzer. These alternative detectors commonly are used for detecting photoelectrons or Auger electrons. Another alternative type of detector is a retarding field analyzer.

In the embodiments described above, the state of contamination of the mirror 23 and filter 25 (situated closest to the vacuum pump 212 and substrate 26) were monitored. Alternatively or in addition, other optical components can be monitored. By monitoring multiple optical components, it is possible to determine separate replacement or cleaning times independently for the respective components, according to their different rates and types of contaminant accumulation.

By applying an apparatus according to the invention to the manufacture of semiconductor devices, it is possible to eliminate having to stop operation of the apparatus to perform routine inspection of the optical components. Eliminating such a step can improve throughput.

In certain configurations discussed above, the state of contamination was detected by determining peak intensities of the detected electron spectrum. Alternatively, it is possible to detect a state of contamination by monitoring variations in a spectrum or changes in the profile of a spectrum.

As an alternative to an LPX, the light-source system 1 can comprise a synchrotron-radiation source or discharge plasma source such as a dense plasma focus or Z-pinch plasma source.

In general, as described above, apparatus according to the present invention make it possible to measure or estimate the state of contamination of optical components, and can be used in conjunction with any of various optical systems. As a result, the replacement and cleaning of the optical components can be performed efficiently.

Whereas the invention has been described in connection with multiple representative embodiments, it will be understood that the invention is not limited to those embodiments. On the contrary, the invention is intended to encompass all modifications, alternatives, and equivalents as may be included within the spirit and scope of the invention, as defined by the appended claims.

What is claimed is:

1. An apparatus for measuring accumulation of a contaminant substance on a surface of an optical component that, during use, is irradiated with radiation, the apparatus comprising contaminant-measuring means situated and configured to (i) detect electrons emitted by the optical component in response to the optical component being irradiated with the radiation; (ii) of the detected electrons, select electrons in a specified energy range; and (iii) obtain a measurement of the detected electrons in the specified energy range so as to obtain a measurement of a corresponding amount of accumulated contaminant substance on the optical component.

2. The apparatus of claim 1, wherein the measurement pertains to a quantity of electrons in the specified energy range.

3. The apparatus of claim 1, wherein said contaminant-measuring means detects electrons emitted from an irradiated surface of the optical component.

4. The apparatus of claim 1, wherein said contaminant-measuring means comprises irradiation means for irradiating the optical component.

5. The apparatus of claim 1, wherein said contaminant-measuring means comprises detection means for detecting electrons emitted from the optical component and producing an output signal having a parameter corresponding to a detected parameter of the electrons within the specified energy range.

6. The apparatus of claim 5, wherein the detected parameter is time of flight of the electrons.

7. The apparatus of claim 1, wherein:

the optical component comprises a surficial material; and the energy range is specified based on a characteristic of the surficial material and on an energy parameter of the radiation.

8. The apparatus of claim 1, wherein the energy range is specified based on a particular contaminant substance predicted to accumulate on the optical component and on an energy parameter of the radiation.

9. The apparatus of claim 1, wherein:

the optical component comprises a surficial material;

said contaminant-measuring means comprises substance-identification means configured to produce a spectrum of detected electrons in the specified energy range, the spectrum being based on the surficial material, the particular contaminant substance that could accumulate on the surficial material, and on an energy parameter of the radiation; and said substance-identification means is configured to identify the contaminant substance by evaluating respective positions and magnitudes of one or more spectral peaks in the spectrum.

10. The apparatus of claim 1, wherein:

said contaminant-measuring means comprises substance-identification means configured to produce a spectrum of detected electrons in the specified energy range, the spectrum being based on the surficial material, the particular contaminant substance that could accumulate on the surficial material, and on an energy parameter of the radiation;

the specified energy range includes a first energy range based on a characteristic of the surficial material and on an energy parameter of the radiation, and a second energy range based on a particular contaminant substance predicted to accumulate on the optical component and on the energy parameter of the radiation; and said substance-identification means is further configured to determine respective numbers of electrons in each of the first and second energy ranges.

11. The apparatus of claim 10, wherein:

said contaminant-measuring means detects electrons in the first energy range so as to produce a first signal, and detects electrons in the second energy range so as to produce a second signal; and said contaminant-measuring means obtains a measurement of a state of contamination of the optical component by comparing the first and second signals.

12. The apparatus of claim 1, wherein:

said contaminant-measuring means comprises detection means for detecting electrons emitted within a specified angular range from the optical component and producing an output signal having a parameter corresponding to a detected parameter of the electrons within the specified energy range; and said contaminant-measuring means comprises means for varying a detection angle of said detection means relative to the optical component.

13. An apparatus for measuring accumulation of a contaminant substance on a surface of an optical component that, during use, is irradiated with radiation, the apparatus comprising:

a detector situated relative to the optical component so as to receive electrons emitted by the optical component in response to the optical component being irradiated with the radiation, the detector being configured to detect the electrons emitted from the optical component and produce a corresponding output signal; and a processor connected to the detector, the processor being configured to select, for data processing by the processor, at least a portion of the output signal corresponding to detected electrons in a specified energy range, and to determine a measurement of the detected electrons in the selected energy range.

14. The apparatus of claim 13, wherein the electrons are selected from the group consisting of photoelectrons and Auger electrons.

15. The apparatus of claim 13, wherein the detector is configured to detect the electrons by time of flight of the electrons.

16. The apparatus of claim 13, wherein the specified energy range is determined based on a characteristic of a material from which the optical component is made and on an energy characteristic of the radiation.

17. The apparatus of claim 16, wherein:

the optical component is a filter or multi-layer mirror; and the material is configured as an outermost layer of the filter or mirror.

18. The apparatus of claim 17, wherein the material can emit inner-shell electrons when irradiated by radiation.

19. The apparatus of claim 13, wherein the radiation is selected from a group consisting of electromagnetic radiation and charged-particle-beam radiation.

20. The apparatus of claim 19, wherein the radiation is X-ray radiation.

21. The apparatus of claim 13, wherein the specified energy range is determined based on a characteristic of a contaminant substance predicted to accumulate on the optical component and on an energy characteristic of the radiation.

22. The apparatus of claim 13, wherein:

the detector comprises a substance identifier that produces a spectrum of electrons within the specified energy range;

the specified energy range is determined based on a characteristic of a material from which the optical component is made and on an energy characteristic of the radiation; and the processor determines peak values within the spectrum and identifies the contaminant substance accumulating on the optical component from the peak values of the spectrum.

23. The apparatus of claim 13, wherein the processor comprises a signal processor configured to process the output signal; a selector connected to the signal processor and configured to determine the specified energy range; a comparator connected to the selector and configured to compare a detected quantity of electrons in the specified energy range to a threshold value; and a memory connected to the comparator and configured to store data corresponding to the threshold value.

24. With respect to an optical system comprising an optical component having a surface that, during use, is irradiated with radiation, a method for measuring accumulation of a contaminant substance on the surface, the method comprising:

(a) directing a beam of radiation to impinge on the surface, the radiation being of a quality that causes the surface to emit electrons in response to being irradiated with the radiation;

(b) detecting the electrons emitted from the surface;

(c) of the detected electrons, selecting electrons in a specified energy range; and (d) measuring the detected electrons in the specified energy range so as to obtain a measurement of a corresponding amount of accumulated contaminant substance on the surface.

25. The method of claim 24, wherein, in step (a), the beam comprises radiation selected from the group consisting of X-rays, ultraviolet light, and charged particles.

26. The method of claim 24, wherein step (d) comprises quantifying the electrons in the specified energy range.

27. The method of claim 24, wherein step (b) comprises detecting electrons selected from the group consisting of photoelectrons and Auger electrons.

28. The method of claim 24, wherein:

step (d) is performed first and second times, wherein the second time is later than the first time and the optical component is used between the first and second times; and the method further comprises comparing respective measurements of electrons obtained in the first and second times.

29. The method of claim 24, wherein step (d) comprises comparing a detected quantity of electrons in the specified energy range to a threshold value, and determining whether the detected quantity exceeds the threshold value.

30. The method of claim 24, wherein step (b) comprises determining time of flight of the electrons.

31. The method of claim 24, wherein step (d) comprises producing a spectrum of detected electrons in the specified energy range, and evaluating respective positions and magnitudes of one or more spectral peaks in the spectrum.

32. The method of claim 31, wherein:

step (c) comprises selecting electrons in a first energy range and selecting electrons in a second energy range, the first energy range being based on a characteristic of a material from which the surface is made, and the second energy range being based on a characteristic of a contaminant substance predicted to accumulate on the optical component during use; and step (d) comprises determining respective numbers of electrons in each of the first and second energy ranges.

33. The method of claim 32, further comprising the step of comparing the respective detected numbers of electrons in the first and second energy ranges.

34. The method of claim 24, wherein step (b) comprises detecting electrons emitted within a specified angular range from the optical component.

35. In an optical apparatus in which a surface of an object is irradiated with X-rays, a device for monitoring accumulation of a contaminant substance on an optical component of the optical apparatus, the device comprising:

an illumination-optical system situated and configured to direct a beam of X-rays, from an X-ray source, along a trajectory leading to the optical component;

a detector situated relative to the optical component so as to receive electrons emitted by the optical component in response to the optical component being irradiated with the beam of X-rays, the detector being configured to detect the electrons emitted from the optical component and produce a corresponding output signal; and a processor connected to the detector, the processor being configured to select at least a portion of the output signal corresponding to detected electrons in a specified energy range, to determine a measurement of the detected electrons in the selected energy range, and to determine an amount of surficial contamination of the optical component with the contaminant substance from the measurement.

36. The apparatus of claim 35, configured as an X-ray microlithography apparatus.

37. The apparatus of claim 36, further comprising a projection-optical system and a reticle, wherein the optical component is the reticle or in the projection-optical system.

38. The apparatus of claim 37, wherein the optical component is an X-ray-reflective mirror.

39. The apparatus of claim 38, further comprising a vacuum chamber enclosing the projection-optical system, the vacuum chamber being connected via an evacuation port to a vacuum pump, wherein the optical component is situated adjacent the evacuation port.

40. The apparatus of claim 39, wherein the optical component is situated in the projection-optical system adjacent a substrate exposed by the X-ray beam.

41. The apparatus of claim 40, wherein the substrate is coated with a resist.

42. In a method for performing microlithography of a substrate with a pattern, defined by a reticle, using an energy beam passing through an optical system, a method for measuring accumulation of a contaminant substance on a surface of an optical component of the optical system, the method comprising:

(a) directing a beam of radiation to impinge on the surface, the radiation being of a quality that causes the surface to emit electrons in response to being irradiated with the radiation;

(b) detecting the electrons emitted from the surface;

(c) of the detected electrons, selecting electrons in a specified energy range; and (d) measuring the detected electrons in the specified energy range so as to obtain a measurement of a corresponding amount of accumulated contaminant substance on the surface.

43. The method of claim 42, wherein the energy beam and radiation beam are X-ray beams.

* * * * *

UNITED STATES PATENT AND TRADEMARK OFFICE
CERTIFICATE OF CORRECTION

PATENT NO. : 6,545,272 B1
DATED : April 8, 2003
INVENTOR(S) : Kondo

It is certified that error appears in the above-identified patent and that said Letters Patent is hereby corrected as shown below:

<u>Column 12,</u>
Lines 21 and 22, "31 a" should be -- 31a --.

Signed and Sealed this

Fourth Day of November, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,545,272 B1
DATED : April 8, 2003
INVENTOR(S) : Kondo

It is certified that error appears in the above-identified patent and that said Letters Patent is hereby corrected as shown below:

Column 12,
Line 21, "31 a" should be -- 31a --.

Signed and Sealed this

Twenty-ninth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,545,272 B1
DATED : April 8, 2003
INVENTOR(S) : Hiroyuki Kondo

It is certified that error appears in the above-identified patent and that said Letters Patent is hereby corrected as shown below:

Column 12,
Line 22, "32 b" should be -- 32b --

Signed and Sealed this

Seventh Day of September, 2004

JON W. DUDAS
*Director of the United States Patent and Trademark Office*